(12) United States Patent
Chen et al.

(10) Patent No.: US 6,620,956 B2
(45) Date of Patent: Sep. 16, 2003

(54) NITROGEN ANALOGS OF COPPER II β-DIKETONATES AS SOURCE REAGENTS FOR SEMICONDUCTOR PROCESSING

(75) Inventors: Ling Chen, Sunnyvale, CA (US); Barry Chin, Saratoga, CA (US)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 10/122,491

(22) Filed: Apr. 12, 2002

(65) Prior Publication Data

US 2003/0097013 A1 May 22, 2003

Related U.S. Application Data

(60) Provisional application No. 60/333,229, filed on Nov. 16, 2001.

(51) Int. Cl.[7] .............................. C07F 1/08; C23C 16/00
(52) U.S. Cl. .................. 556/110; 556/113; 427/587; 427/593
(58) Field of Search .................. 556/110, 113; 427/587, 593

(56) References Cited

U.S. PATENT DOCUMENTS

| | | | | |
|---|---|---|---|---|
| 5,021,187 A | * | 6/1991 | Harriott et al. | 252/186.38 |
| 5,084,201 A | * | 1/1992 | Greco | 252/182.12 |
| 5,225,561 A | | 7/1993 | Kirlin et al. | 546/256 |
| 5,252,247 A | * | 10/1993 | Greco et al. | 252/182.12 |
| 5,368,768 A | * | 11/1994 | Greco et al. | 505/510 |
| 5,464,666 A | | 11/1995 | Fine et al. | 427/576 |
| 5,820,664 A | | 10/1998 | Gardiner et al. | 106/287.17 |
| 5,840,897 A | | 11/1998 | Kirlin et al. | 546/2 |
| 6,034,258 A | | 3/2000 | Kristen et al. | 556/12 |
| 6,110,529 A | | 8/2000 | Gardiner et al. | 427/250 |
| 6,126,996 A | | 10/2000 | Kirlin et al. | 427/252 |
| 6,218,518 B1 | | 4/2001 | Baum et al. | 534/15 |
| 6,277,436 B1 | | 8/2001 | Stauf et al. | 427/126.3 |
| 6,284,654 B1 | | 9/2001 | Roeder et al. | 438/681 |
| 6,369,256 B1 | * | 4/2002 | Chi et al. | 556/113 |
| 6,534,666 B1 | | 3/2003 | Zorich et al. | 556/41 |
| 2002/0004293 A1 | | 1/2002 | Soininen et al. | 438/584 |

FOREIGN PATENT DOCUMENTS

| | | |
|---|---|---|
| DE | 42 02 889 A1 | 8/1993 |
| EP | 0 369 297 A1 | 5/1990 |
| WO | WO 96/40690 | 12/1996 |

OTHER PUBLICATIONS

Graddon et al., J. Inorg. Nucl. Chem., vol. 37, No. 2, pp. 469–472 (1975).*
"Journal of the Electrochemical Society" from A Journal for Solid–State and Electrochemical Science and Technology, vol. 145, No. 8, Aug. 1998, by Per Martensson and Jan–Otto Carlsson, pp. 2926–2931.
"Atomic Layer Deposition of Copper Seed Layers" from Electrochemical and Solid–State Letters, 3 (10), 2000, by Rai Solanki and Balu Pathangey, pp. 479–480.
Atomic Layer Epitaxy of Copper on Tantalum: from Chemical Vapor Deposition by Per Martensson and Jan–Otto Carlsson, pp. 45–50.

(List continued on next page.)

Primary Examiner—Porfirio Nazario-Gonzalez
(74) Attorney, Agent, or Firm—Moser, Patterson & Sheridan, LLP

(57) ABSTRACT

Nitrogen containing analogs of Copper II β-diketonates which analogs are more stable source reagents for copper deposition when substantially free of solvents of excess ligands. The nitrogen containing analogs replace —O— with —N(R")— wherein R" is an alkyl group having from one to four carbon atoms. Replacement of each —O— is preferred although replacement of one —O— per cyclic ring is sufficient to improve stability of the copper source reagents. The source reagent can be purified by sublimation to remove solvents and excess ligands prior to semiconductor processing.

10 Claims, 1 Drawing Sheet

OTHER PUBLICATIONS

"Synthesis and properties of some β–diketimines derived from acetylacetone, and their metal complexes," from Canadian Journal of Chemistry, vol. 46, Jun. 1, 1968, No. 11, by S.G. McGeachin, pp. 1903–1912.

Abstract Entitled "New copper and nickel complexes with MO2N2 and MN4 coordination units" by Kurbatov, V.P., et al. from Tezisy Dokl.—Vses. Chugaevskoe Soveshch. Khim. Kompleksn. Soedin, 12$^{th}$ (1975), vol. 3, 369.

Abstract Entitled "Thermodynamics of metal–ligand bond formation. XIII. Adducts of aliphatic diamines with copper (II) complexes of fluorinated β–diketones" by Graddon, D.P., et al. from J. Inorg. Nucl. Chem. (1975), 37 (2), 469–72.

Abstract Entitled "Structural and electronic effects on the polarographic half–wave potentials of copper (II) chelate complexes" by Patterson, G.S., et al. from Bioinorg. Chem. (1975), 4 (3), 257–75.

Abstract Entitled "Synthesis and properties of some β–diketimines derived from acetylacetone, and their metal complexes" by McGeachin, S.G. from Can. J. Chem. (1968), 46 (11), 1903–12.

Abstract Entitled "4–N, N–di–ethylamino–3–penten–2–one complexes of some metals of first transition series" by Ismail, Muhammad, et al. from J. Chem. Soc. Pak. (1998), 20 (3), 182–185.

Abstract Entitled "Behavior of copper and nickel chelates of β–ketoimines and related compounds in electron capturing detector–gas chromatography (ECD–GC)" by Miyazaki, Motoichi, et al. from Chem. Pharm. Bull. (1979), 27 (4), 1045–8.

Abstract Entitled "Solution stereochemistry of four–coordinate bis (chelate) metal (II) complexes. Further experimental results and a summary of stereochemical trends" by Gerlach, D.H., et al. from Inorg. Chem. (1970), 9 (3), 558–94.

Abstract Entitled "Cu(thd) 2 as copper source in atomic layer epitaxy" by Martensson, P., et al. from Chemical Vapor Deposition. Proceedings of the Fourteenth International Conference and EUROCVD–11, 1997, pp. 1529–1536.

Abstract Entitled "Liquid precursor mixtures for deposition of multicomponent metal containing electronic materials" by Senzaki, Yoshihide, et al. from Eur. Pat. Appl., 8 pages, U.S. 6238734.

Abstract Entitled "Studies of metallic thin film growth in an atomic layer epitaxy reactor using M(acac) 2 (M equals Ni, Cu, Pt) precursors" by Utriainen, Mikko, et al. from Applied Surface Science v 157 n 3 2000, pp. 151–158.

Abstract Entitled "Atomic layer epitaxy of copper. Growth and selectivity in the Cu(II)–2,2,6,6–tetramethyl–3,5–heptanedionate/H 2 process" by Martensson, P., et al. from Journal of the Electrochemical Society, vol. 145, No. 8, Aug. 1998, pp. 2926–2931.

Abstract Entitled "Comparative study of atomic layer deposition and low–pressure MOCVD of copper sulfide thin films" by Goossens, A., et al. from J. Phy. IV JP vol. 11, No. 3, 2001, pp. Pr31147–Pr31152.

Abstract Entitled "Polycrystalline Cu(InGa) Se 2 thin–film solar cells with ZnSe buffer layers" by Ohtake, Yasutoshi, et al. from Japanese Journal of Applied Physics, Part 1: Regular Papers & Short Notes & Review Papers v 34 n 11 Nov. 1995, pp. 5949–5955.

Abstract Entitled Selflimiting adsorption of precursors for chemical vapor deposition of oxide superconductors by Oda, S., et al. from Physica C: Superconductivity v 185–89 pt 3 Dec. 1, 1991, pp. 2001–2002.

Abstract Entitled "Epitaxial growth of Bi Sr Ca Cu O superconducting thin films by metalorganic chemical vapor deposition" by Sugimoto, T., et al. from Applied Physics Letters, vol. 57 No. 9, Aug. 27, 1990, pp. 928–930.

XP–002229349 "Effect of the type of donor atoms on the structure and properties of copper (II), nickel (II) and iron (II) chelates with .beta.–diketone derivations" from Doklady Akademii Nauk SSSR, vol. 257, No. 1, 1981, by Pilipenko, et al., pp. 153–155.

XP–002229350 "The mutual influence of ligands in transition metal bis–chelates" from Theochem, vol. 3, No. 1–2, 1981, by Pilipenko, et al., pp. 155–162.

XP–002229351 "Electronic structure of nickel (II) and copper (II) .beta.–diketone complexes" from Poverkhnost, vol. 8, 1997, by I. L'Vov and Y. Ivanov, pp. 5–10.

PCT Search Report dated Mar. 4, 2003 for PCT/US02/36301.

* cited by examiner

NITROGEN ANALOGS OF COPPER II β-DIKETONATES AS SOURCE REAGENTS FOR SEMICONDUCTOR PROCESSING

CROSS-REFERENCE TO RELATED APPLICATIONS

This application claims benefit of United States provisional patent application serial No. 60/333,229, filed on Nov. 16, 2001, which is herein incorporated by reference.

BACKGROUND OF THE INVENTION

1. Field of the Invention

The present invention generally relates to thermally decomposable organometallic source reagents that are useful for the formation of metal films on substrates. More specifically, the invention relates to nitrogen analogs of Copper II β-diketonates as source reagents useful in semiconductor processing for deposition of films comprising copper.

2. Description of the Related Art

Thermal decomposition of organometallic source reagents is a particularly attractive method for forming metal films because it is readily scaled up to production runs and because the electronics industry has a wide experience and an established equipment base in the use of vaporization and decomposition technology.

Semiconductor processing requires source reagents that are sufficiently volatile to permit their gas phase transport into the decomposition reactor. The source reagent must decompose in the reactor to deposit only the desired element (s) at the desired growth temperature on the substrate. Premature gas phase reactions are desirably avoided, and it generally is desired to controllably deliver source reagents into the reactor to effect correspondingly close control of film stoichiometry.

Many potentially useful metal compounds are not well suited for semiconductor processing. For example, some potential source reagents are solids that are amenable to sublimation for gas-phase transport into the reactor, however the sublimation temperature may be very close to the decomposition temperature. Accordingly, the reagent may begin to decompose in the lines leading to the reactor, and it then becomes difficult to control the stoichiometry of the deposited films.

Solvents such as tetrahydrofuran or diethyl ether or excess ligands may enhance vaporization of source reagents by forming a complex. However, release of the solvents or excess ligands during semiconductor processing can result in unpredictable variations in processing conditions.

Accordingly, there is a continuing search in the art for improved source reagent compositions which are more amenable to vaporization to form the source component vapor for semiconductor processes.

SUMMARY OF THE INVENTION

The present invention provides nitrogen containing analogs of Copper II β-diketonates which analogs are stable source reagents for copper deposition when separated from solvents and excess ligands. The nitrogen containing analogs replace —O— with —N(R")— wherein R" is an alkyl group having from one to four carbon atoms. Replacement of each —O— is preferred although replacement of one —O— per cyclic ring is sufficient to improve stability of the copper source reagents. The nitrogen containing analogs can be separated from solvents and excess ligands by sublimation.

DETAILED DESCRIPTION OF THE INVENTION

The present invention is based on the discovery of improved stability of nitrogen containing analogs of Copper II β-diketonates which analogs are excellent source reagents for copper deposition when solvents and excess ligands are substantially removed, such as by sublimation as described by S. G. McGeachin, "Synthesis And Properties Of Some ∃-Diketimines Derived From Acetylacetone, And Their Metal Complexes", Canadian Journal of Chemistry Vol. 46, No. 11, June 1968. The nitrogen containing analogs replace —O— with —N(R")— wherein R" is an alkyl group having from one to four carbon atoms. Replacement of each —O— in the analog is preferred although replacement of one —O— per cyclic ring is sufficient to improve stability of the copper source reagents when separated from solvent and excess ligands. Purification by sublimation substantially removes solvents and excess ligands in comparison to solvent extraction methods.

Figure 1:
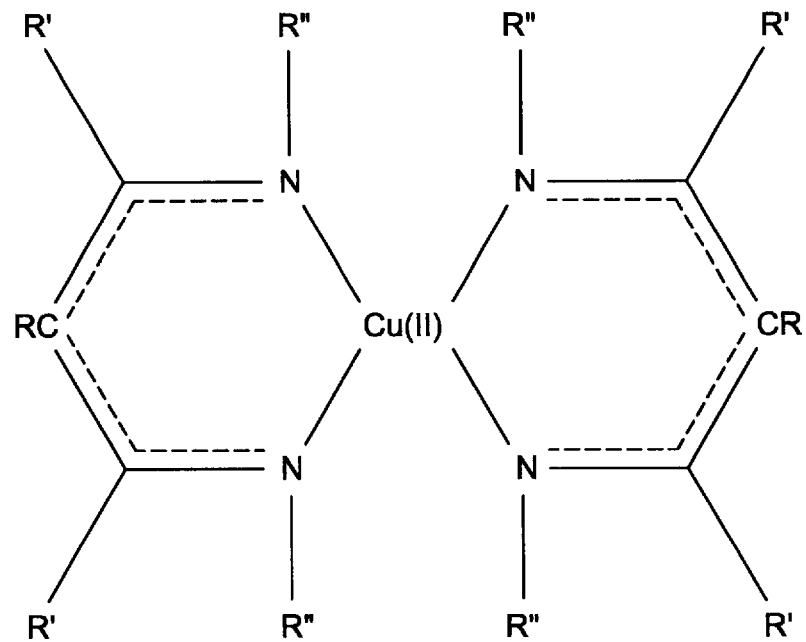
FIG. 1 is a generic structure for Copper II β-diketiminates of the present invention wherein R and R' are hydrogen and R" is an alkyl group having from one to four carbon atoms.

FIG. 1 illustrates a generic structure for Copper II β-diketiminates. Compounds having the structure of FIG. 1 are similar to Copper II β-diketonates wherein R is typically hydrogen or methyl, and R' is typically hydrogen, an alkyl group, an aryl group, an alkylaryl group, an alkoxy group, or combinations thereof. For the present invention R and R' are hydrogen and R" is an alkyl group having from one to four carbon atoms. Preferably, R" is ethyl.

Figure 2:
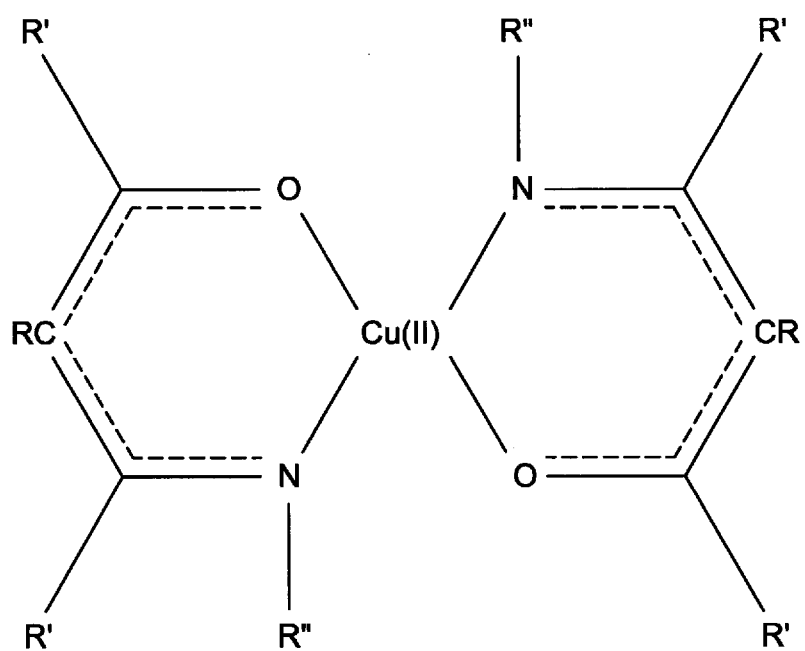
FIG. 2 is a generic structure for Copper II β-ketoiminates of the present invention wherein R and R' are hydrogen and R" is an alkyl group having from one to four carbon atoms.

FIG. 2 illustrates a generic structure for Copper II β-ketoiminates. Compounds having the structure of FIG. 2 are similar to Copper II β-diketonates wherein R is typically hydrogen or methyl, and R' is typically hydrogen, an alkyl group, an aryl group, an alkylaryl group, an alkoxy group, or combinations thereof. For the present invention R and R' are hydrogen and R" is an alkyl group having from one to four carbon atoms. Preferably, R" is ethyl.

The various source reagents employed in the invention may be readily made by conventional synthetic techniques, including those more fully described in S. G. McGeachin, "Synthesis And Properties Of Some β-Diketimines Derived From Acetylacetone, And Their Metal Complexes", Canadian Journal of Chemistry Vol. 46, No. 11, June 1968, or German Patent Publication 42 02 889 laid open on Aug. 5, 1993, the disclosures of which are incorporated herein by reference. However, purification of the source reagents by solvent extraction does not adequately remove solvents and excess ligands that may complex with the source reagents. The remaining impurities can substantially impair performance of the source reagents. The source reagents are improved by more rigorous purification methods such as separation of the purified source reagent by sublimation. Other methods for purification can be used if residual solvents or excess ligands are removed.

Hypothetical Example

According to the procedure described in German Patent Publication 42 02 8894, N,N'-diethyl-1,3-propanediketimine (0.17 mol) in 200 mL pentane is introduced into a 500-mL flask. Then 100 mL of a 1.6 M solution of n-butyllithium in hexane is added slowly dropwise with stirring. Then 0.42 g (0.0032 mol) of copper dichloride is reacted with 2 molar equivalents (0.0063 mol) of the lithium N,N'-diethyl-1,3-propanediketiminate in diethyl ether. The precipitated lithium chloride is filtered off. The volatile components are evaporated off from the remaining solution in a vacuum, and then the residue is purified by washing with pentane.

For the present invention, the purified residue is further purified by sublimation at 100–150° C. at about 10 mTorr to remove solvents and excess N,N'-diethyl-1,3-propanediketimine.

While the invention has been described herein with reference to specific embodiments, features and aspects, it will be recognized that the invention is not thus limited, but rather extends in utility to other modifications, variations, applications, and embodiments, and accordingly all such other modifications, variations, applications, and embodiments are to be regarded as being within the spirit and scope of the invention.

What is claimed is:

1. A source reagent having the structure of FIG. 1 or FIG. 2, wherein R and R' are hydrogen and R" is an alkyl group having from one to four carbon atoms, wherein the source reagent is substantially free of solvents and excess ligands.

2. The source reagent of claim 1, wherein R" is ethyl.

3. The source reagent of claim 1, wherein the source reagent has the structure of FIG. 1.

4. The source reagent of claim 1, wherein the source reagent has the structure of FIG. 2.

5. The source reagent of claim 1, wherein the source reagent has the structure of FIG. 1 and R" is ethyl.

6. A source reagent having the structure of FIG. 1, wherein R and R' are hydrogen and the source reagent is purified by sublimation.

7. The source reagent of claim 6, wherein R" is ethyl.

8. A source reagent having the structure of FIG. 2, wherein the source reagent is purified by sublimation.

9. The source reagent of claim 8, wherein R" is ethyl.

10. A method for making a source reagent of FIG. 1 or FIG. 2 wherein R and R' are hydrogen and R" is an alkyl group having from one to four carbon atoms, comprising sublimation of the source reagent to remove solvents or excess ligands prior to semiconductor processing.

* * * * *